US00PP09288P

United States Patent [19]

DeVor

[11] Patent Number: Plant 9,288

[45] Date of Patent: Sep. 19, 1995

[54] CLIMBING HYBRID TEA ROSE PLANT NAMED 'DEVBILL'

[75] Inventor: William DeVor, Avondale, Ariz.

[73] Assignee: DeVor Nurseries, Inc., Watsonville, Calif.

[21] Appl. No.: 310,711

[22] Filed: Sep. 21, 1994

[51] Int. Cl.[6] ..... A01H 5/00

[52] U.S. Cl. ..... Plt./5

[58] Field of Search ..... Plt. 18, 5, 6, 19, 20

*Primary Examiner*—Howard J. Locker

*Attorney, Agent, or Firm*—Christie, Parker & Hale

[57] ABSTRACT

A new Hybrid Tea rose plant which is a climbing sport of the variety 'Sheer Elegance'.

1 Drawing Sheet

SUMMARY OF THE INVENTION

The present invention relates to a new and distinct variety of rose plant of the hybrid tear rose class which was discovered in a cultivated planting of the variety 'Sheer Elegance' varietal denomination 'Twobe' (U.S. Plant Pat. No. 7,901) as a climbing sport. The varietal denomination of this new rose is 'Devbill'.

Among the novel characteristics possessed by this new variety which distinguish it from its parent are its more vigorous growth habit which classifies the new variety as a climber.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Climbing sport of the variety 'Sheer Elegance' (varietal denomination 'Twobe' U.S. Plant Pat. No. 7,901).

Class: Climbing Hybrid Tea.

The following is a detailed description of my new variety, of new specimens grown outdoors in Watsonville, Calif. in the month of August. The color terminology used is in accordance with the Royal Horticultural Society Colour Chart (RHSCC), and refers to plate numbers in the aforementioned color chart. Phenotypic expression may vary depending on light, environmental and cultural conditions. Where general terms such as average, normal, medium, ordinary, etc. are used, the characteristics so described are not considered distinguishing.

FLOWER

Blooming habit: Recurrent.

A. Bud:

(1) *Size.*—Medium.

(2) *Form.*—Pointed, tapering, slender.

(3) *Color.*—When sepals first divide, bud color is near 61B.

(4) *Sepals.*—Just cover bud, some sepals are foliaceous, about 3 to 3.5 cm long. Color: Near 137D.

(5) *Peduncle.*—Length: About 8–9 cm. Aspect: Somewhat straight to curvy, few small prickles. Strength: Erect, sturdy. Color: Near 144B with near 60D.

(6) *Bracts.*—Number 2; broadly lanceolate with caudate apex, 8 to 9 cm below calyx; near 61C at base wtih near 144B at edges.

B: Bloom:

(1) *Size.*—Average size when fully expanded — about 14 to 15 cm.

(2) *Borne.*—Singly, one to a stem.

(3) *Form.*—Informal, becoming ruffled at maturity.

(4) *Petalage.*—Number of petals under normal conditions — about 24 to 30.

(5) *Color.*—⅓ to ½ open: Outer petals — Top surface near 50A with near 36B along outer edge. Adjacent base near 48D and at base near 5A. Undersurface — Outer edge near 58B, balance near 48C. Adjacent base near 49D and at base near 6C. Inner petals — Top surface outer edge near 58B. Top surface near 68D, adjacent base near 38D and at base near 5A. Undersurface outer edge near 61C, with balance near 69A. Adjacent base near 27D and at base near 5C. Base of petals (point of attachment), near 5A. General tonality from a distance: Coral. Fully open bloom: Outer petals — Top surface outer edge near 65A with top near 52A. Adjacent base near 36B and at base near 4B. Undersurface — outer edge near 58B, balance near 62D, adjacent base near 62D and at base near 1C. Inner petals — Top surface outer edge near 62C with balance near 58C, adjacent base near 69A and at base near 3B. Undersurface — outer edge near 61D with balance near 73D, adjacent base near 49D and at base near 3C. Base of petals (point of attachment) — Near 3B. General tonality from a distance: Coral. Color change: As bloom ages, color lightens, petal top surface near 65D, petal undersurface near 155D. General tonality at a distance: Light pink.

C. Petals:

(1) *Texture.*—Thick.

(2) *Appearance.*—Inside leathery and outside smooth.

(3) *Form.*—Ovoid to round.

(4) *Arrangement.*—Regularly arranged, imbricated and informal at maturity.

(5) *Petaloids.*—Few.
(6) *Fragrance.*—Slight.
(7) *Persistence.*—Persist.
(8) *Lasting quality.*—Very long on plant under coastal California conditions and as cut flower.

REPRODUCTIVE ORGANS

A. Stamens:
(1) *Color.*—Near 52B, base near 15C.
(2) *Arrangement.*—Regularly arranged.
(3) *Anthers.*—Color near 23C.
(4) *Filaments.*—Color near 23C.
(5) *Pollen.*—Color near 23C.

B. Pistils
(1) *Styles.*—Bunched, even, short.
(2) *Stigmas.*—Color near 23C.

C. Characteristics of hips: Obovate, about 3 to 3.5 cm long by about 2 to 3 cm wide, near 169C, some seeds protrude.

PLANT

A. Form: Upright, branching.

B. Growth: Very vigorous, height attained about 315 to 345 cm at first season.

C. Foliage: Compound 3 to 7 leaflets.
(1) *Size.*—Large.
(2) *Quality.*—Abundant.
(3) *Color.*—New foliage — upper side near 200B, underside near 183B; mature foliage — upper side near 147A, underside near 147C.
(4) *Shape.*—Oval.
(5) *Texture.*—Semi-glossy, leathery, underside dull.
(6) *Edge.*—Serrated.
(7) *Serration.*—Serrate.
(8) *Leaf stem.*—Color — medium green.
(9) *Stipules.*—Long, slightly curved inward.
(10) *Rachis.*—Small prickles.
(11) *Petioles.*—Top near 146B, underside near 146C.
(12) *Auricle.*—Slender.
(13) *Resistance to disease.*—Good resistance to mildew, rust and blackspot.

D. Wood
(1) *New wood.*—Color near 183B.
(2) *Old wood.*—Color near 146C, bark rough.

E. Thorns:
*Quality.*—Profuse on main stalk and lateral from stalk.
*Form.*—Wide at base then thin, slightly curved downward.
*Length.*—Long.
*Color.*—Near 59A when young.
*Position.*—Irregular.
*Prickles.*—Profuse.

F. Winter hardiness: Excellent winter hardiness under California coastal conditions.

I claim:

1. A new and distinct variety of rose plant of climbing Hybrid Tea rose class, substantially as shown and described.

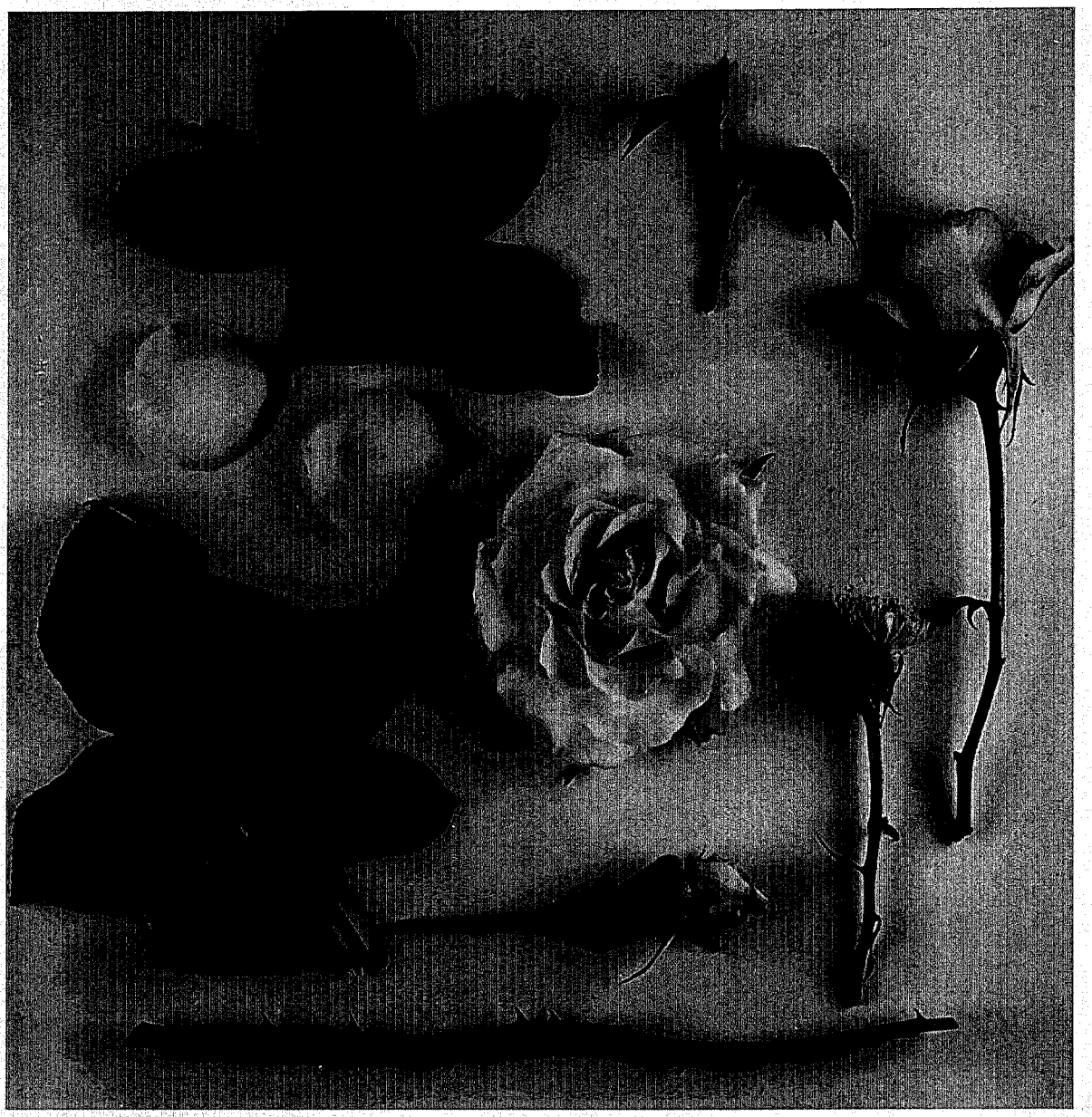

* * * * *